United States Patent [19]

Phillips et al.

[11] Patent Number: 4,956,284

[45] Date of Patent: Sep. 11, 1990

[54] PROCESS FOR PRODUCING 4-(2-METHOXYETHYL)-PHENYL-GLYCIDYL ETHER AND/OR METOPROLOL

[75] Inventors: Gareth T. Phillips; Brian W. Robertson, both of Kent, Great Britain; Mauro A. Bertola, Delft, Netherlands; Hein S. Koger, Spaarbdan, Netherlands; Arthur F. Marx, Delft, Netherlands; Peter D. Watts, Kent, Great Britain

[73] Assignee: Gist-Brocades N.V., Delft, Netherlands

[21] Appl. No.: 826,791

[22] Filed: Feb. 6, 1986

Related U.S. Application Data

[63] Continuation-in-part of Ser. No. 735,079, May 16, 1985, abandoned.

[30] Foreign Application Priority Data

Feb. 13, 1985 [NL] Netherlands ......................... 8503666

[51] Int. Cl.$^5$ ....................... C12P 17/02; C12P 13/00; C12N 1/12; C12R 1/365
[52] U.S. Cl. ........................... 435/123; 435/128; 435/253.2; 435/253.3; 435/253.1; 435/863; 435/872; 435/874
[58] Field of Search ................. 549/555; 435/863, 872, 435/874, 822, 123, 248, 253, 118, 119, 120, 128, 129, 253.2, 253.3, 253.1

[56] References Cited

U.S. PATENT DOCUMENTS

| | | | |
|---|---|---|---|
| 4,085,136 | 4/1978 | Tucker | 564/171 |
| 4,368,267 | 1/1983 | Hou et al. | 435/822 X |

FOREIGN PATENT DOCUMENTS

| | | | |
|---|---|---|---|
| 9216595 | 12/1984 | Japan | 435/123 |
| 0291163 | 6/1965 | Netherlands | 435/123 |

OTHER PUBLICATIONS de Smet et al., "*Pseudomonas oleovorans*"as a Tool in Bioconversions of Hydrocarbons: Growth, Morphology and Conversion Characteristics in Different Two Phase Systems, *Enz Microb Techol.*, 5, 352–360, 1983.

Gelb et al., "Cytochrome P450$_{cam}$ Catalized Epoxidation of Dehydrocamphor", *Biochem. and Biophy. Res. Comm.* 104, 853–858, 1982.

Morrison et al., *Organic Chemistry* 1980, pp. 119 and 130.

Ohta et al., *Agric. Biol. Chem.* 1979, vol. 43, pp. 2099–2104.

ATCC Catalog, 1985, pp. 52 and 150.

*Primary Examiner*—Elizabeth C. Weimar
*Assistant Examiner*—Irene Marx
*Attorney, Agent, or Firm*—Bierman and Muserlian

[57] ABSTRACT

A process for the preparation of metoprolol in a stereospecific form or a non-toxic, pharmaceutically acceptable acid addition salt thereof and/or a stereospecific form of 4-(2-methoxyethyl)-phenyl glycidyl ether which comprises subjecting 4-(2-methoxyethyl)-phenyl allyl ether to the action of a microorganism having the ability for stereoselective epoxidation of 4-(2-methoxyethyl)-phenyl allyl ether into 4-(2-methoxyethyl)-phenyl glycidyl ether having at least 80% by weight the S configuration, at least partly separating 4-(2-methoxyethyl)-phenyl glycidyl ether and/or reacting 4-(2-methoxyethyl)-phenyl glycidyl ether with isopropylamine and at least partly separating metoprolol and/or converting metoprolol into its non-toxic, pharmaceutically acceptable acid addition salt.

13 Claims, 3 Drawing Sheets

PROCESS FOR PRODUCING 4-(2-METHOXYETHYL)-PHENYL-GLYCIDYL ETHER AND/OR METOPROLOL

PRIOR APPLICATION

This application is a continuation-in-part application of corresponding U.S. Patent Application Serial No. 735,079 filed May 16, 1985, now abandoned.

STATE OF THE ART

It is commonly known that many biologically active compounds exist as a mixture of stereoisomers (optically active isomers) and most frequently, these mixtures are used as such in agricultural and pharmaceutical applications. The major reason is that the separation costs still exceed the potential advantage of increase in activity. Usually, the required biological activity resides in one stereoisomer so that at best the potency of the mixture is reduced to half. However, it is apparent that modern pharmacologists are becoming increasingly aware of other implications of administering mixtures wherein one stereoisomer is regarded as an impurity that may not have the desired therapeutic effect but may well have other unwanted physiological effects including toxicity. Some examples are cited to illustrate the association of biological activity with single stereoisomers.

Within the pharmaceutical area, most of the β-adrenergic blocking agents are sold as mixtures although the activity resides in one stereoisomer. In one instance, a drug known as labetalol has a combined α-adrenegic blocking and β-adrenergic blocking action that has been shown to be attributed to two separate pairs of isomers from the mixture of four. N. Toda et al reported [J. Pharmacol. Exp. Ther., Vol. 207 (1978) p. 311] that (−)-metoprolol is 270 to 380 times more potent thant (+)-metoprolol in attenuating the response of rabbit atria and tracheal muscles to isoproterenol (a β-adrenoreceptor stimulant).

Current routes to single stereoisomer β-blockers generally involve chemical resolutions or rather lengthy chemical syntheses from stereoisomeric active precursors which are for example described in U.S. Pat. No. 4,408,063 and in J. Org. Chem. Vol. 41 (1976), p. 3121 by Weinstok et al. Thus, these described processes to prepare analogously the S enantiomer (optically active stereoisomer) of metoprolol are not economically advantageous in industrial application. The ability of microorganisms to convert stereospecifically short-chain alkenes of 2 to 4 carbon atoms into their corresponding epoxyalkanes in a gas/solid or in a two-liquid phase bioreactor is demonstrated by Tramper et al. [3rd European Congress on Biotechnology, Munchen, 10–14 Sept. 1984]. Another example of the microbiological preparation cf epoxyalkanes is disclosed in U.S. Pat. No. 4,106,986 describing the conversion of straight-chain 1-alkenes of 2 to 20 carbon atoms into 1,2-epoxyalkanes. In European Patent Application No. 0099609, examples are given of the conversion of propene and 1-octene into their corresponding epoxyalkanes. However, the conversion of substituted alkenes such as 4-(2-methoxyethyl)-phenyl allyl ether can in no way be deduced from these known processes which are only applicable to straight or sometimes branched alkanes.

OBJECTS OF THE INVENTION

It is an object of the invention to provide an efficient process for the preparation of such stereoisomers which may be carried out on an industrial scale in an economically attractive way.

This and other objects and advantages of the invention will become obvious from the following detailed description.

THE INVENTION

The process of the invention for the preparation of metoprolol in a stereospecific form or a non-toxic, pharmaceutically acceptable acid addition salt thereof and/or a stereospecific form of 4-(2-methoxyethyl)-phenyl glycidyl ether comprises subjecting 4-(2-methoxyethyl)-phenyl allyl ether to the action of a microorganism having the ability for stereoselective epoxidation of 4-(2-methoxyethyl)-phenyl allyl ether into 4-(2-methoxyethyl)-phenyl glycidyl ether having at least 80% by weight the S configuration, at least partly separating 4-(2-methoxyethyl)-phenyl glycidyl ether and/or reacting 4-(2-methoxyethyl)-phenyl glycidyl ether with isopropylamine and at least partly separating metoprolol and/or converting metoprolol into its non-pharmaceutically acceptable acid addition salt. Preferably, the process is carried out so that by selecting proper microorganisms, the metoprolol at least 90% by weight is formed in the S configuration.

Examples of suitable microorganisms are for example bacteria belonging to the genera Rhodococcus, Mycobacterium, Nocardia and Pseudomonas. The microorganisms are optionally immobilized with polymer gel. The microorganisms for the epoxidation of 4-(2-methoxy ethyl)-phenyl allyl ether include cultures of species *Nocardia corallina* (an example of this species is deposited in the ATCC under the accession number of 31338), species *Rhodococcus sp* (an example of this species is deposited in the NCIB under the accession number of 11277), species *Mycobacterium rhodochrous* (an example of this species is deposited in the NCIB under the accession number of 703), species *Rhodoccus equi* (an example of this species is deposited in the NCIB under the accession number of 12035), species *Pseudomonas aeruginosa* (an example of this species is deposited in the NCIB under the accession number 12036), species *Pseudomonas oleovorans* (an example of this species is deposited in the ATCC under the accession number 29347), species *Pseudomonas putida* (an example of this species is deposited in the NCIB under the accession number of 9571) and species *Pseudomonas aeruginosa* (an example of this species is deposited in the NCIB under the accession number of 8704).

In practicing the preferred embodiment of the process o the invention, a microorganism having the ability to convert 4-(2-methoxyethyl)-phenyl allyl ether into 4-(2-methoxyeth glycidyl ether having at least 90% by weight the S configuration ha to be selected from the above-mentioned microorganism to be culture for 0.5 to 10 days whereafter the bacterial cells are collected from the culutre solution, the cells are suspended in a liquid nutrient medium and 4-(2-methoxyethyl)-phenyl allyl ether is subjected to the action of the cells.

The microorganisms used in the present invention showing the epoxidation activity, have to be cultured for about 0.5 to 10 days, whereafter the cells are suspended in a liquid nutrient medium, preferably a minimal liquid nutrient medium, and 4-(2-methoxyethyl)- phenyl allyl ether is subjected to the action of the cells. After the cultivation of about 0.5 to 10 days, the cells may be isolated from the culturing medium before suspending the cells in the minimal liquid nutrient medium. To grow the microorganisms used f the stereo selective epoxidation of 4-(2-methoxyethyl)-phenyl ally ether, ordinary culture mediums containing an assimilable carbon source [for example glucose, lactate, hydrocarbons like tetradecane ($C_{14}$), etc.], a nitrogen source [for example ammonium sulfate, ammonium nitrate, ammonium chloride, etc.], with an agent for an organic nutrient source [for example yeast extract, malt extract, peptone, meat extract, etc.] and an inorganic nutrient source [for example phosphate, magnesium, potassium, zinc, iron° and other metals in trace amounts]may be used. Optionally an inducer, for example diethoxymethane, is added to the culture medium. A tempera ture between 0 and 45° C. and a pH between 3.5 and 9 is maintained during the growth of the microorganisms. Preferably the microorganisms are grown at a temperature between 20 and 37° C. and at a pH between 5 and 8.

The aerobic conditions required for the growth of the microorganisms can be provided by any of the well established procedures provided that the supply of oxygen is sufficient to meet the metabolic requirement of the microorganisms. This is most conveniently achieved by supplying a gaseous oxygen, preferably in the form of air. During the conversion of 4-(2-methoxyethyl)-phenyl allyl ether into 4-(2-methoxyethyl)-phenyl glycidyl ether, the microorganisms can be in a growing stage using an abovementioned ordinary culture medium and the microorganisms may be supplemented with a cosubstrate.

Preferably during the conversion of 4-(2-methoxyethyl)-phenyl allyl ether into 4-(2-methoxyethyl)-phenyl glycidyl ether, the microorganisms can be held in a substantially non-growing stage us: a minimal culture medium such as an ordinary culture medium containing an assimilable carbon source when required [for example glucose, lactate, hydrocarbons like tetradecane ($C_{14}$) etc.], a nitrogen source when required [for example ammonium sulfate, ammonium nitrate, ammonium chloride, etc.], with an agent for an organic nutrient source when required [for example yeast extract, malt extract, peptone, meat extract, etc.] and an inorganic nutrient source when required [for example phosphate, magnesium, potassium, zinc, iron and other metals in trace amounts]. The microorganisms can be kept in the non-growing stage for example under exclusion or the assimilable carbon source or under exclusion of the nitrogen source and a temperature between 0 and 45° C. and a pH between 3.5 and 9 is maintained during this stage. Preferably, the microorganisms are held at a temperature between 20 and 37° C. and a pH between 5 and 8. The aerobic conditions required during this stage can be provided by the abovementioned procedures, provided that the supply of oxygen is sufficient to meet the metabolic requirement of the microorganisms but also to convert 4-(2-methoxyethyl)-phenyl allyl ether into 4-(2-methoxyethyl)-phenyl glycidyl ether. The 4-(2-methoxyethyl)-phenyl glycidyl ether produced by the microorganisms as mentioned above can be recovered and purified according to any of the well established procedures.

(−)-4-(2-methoxyethyl)-phenyl glycidyl ether, (+)-4-(2-methoxyethyl)-phenyl glycidyl ether or mixtures thereof the invention can be converted into (+)-metoprolol, (−)-metoprolol or mixtures thereof, respectively, by the chemical reaction with isopropylamine. An example of the reaction to form β-adrenergic receptor blocking agents with the absolute (S)-configuration from aryl glycidyl ethers with the absolute (S)-configuration is described in the German Patent Application No. 2,453,324.

Especially mixtures with a predominant amount of the compound (−)-metoprolol can be advantageously used in pharmaceutical products. Preferably those compounds having at least 80% and more preferably at least 90%, by weight the S configuration can be used in pharmaceutical products An example for a pharmaceutically acceptable salt of metoprolol is: metoprolol tartrate prepared from metoprolol and L-tartaric acid. The optical purity as will be mentioned in the specification is represented as percent enantiomeric excess: S-R/S+R Referring now to the drawings:

FIG. 1 shows the partial pmr spectra of (+) and (±)-4-(2-methoxyethyl)-phenyl glycidyl ether in the presence of europium shift reagent.

A: (±) or (+)-4-(2-methoxyethyl)-phenyl glycidyl ether without shift reagent

B: (±)-4-(2-methoxyethyl)-phenyl glycidyl ether with Eμ (hfc)3; Ratio Eμ (hfc)3 / (±)-4-(2-methoxyethyl)-phenyl glycidyl ether =0.10

C: (+)-4-(2-methoxyethyl)-phenyl glycidyl ether with Eμ (hfc)3; Ratio Eμ (hfc)3 / (+)-4-(2-methoxyethyl)-phenyl glycidyl ether =0.12

Figure 1A:
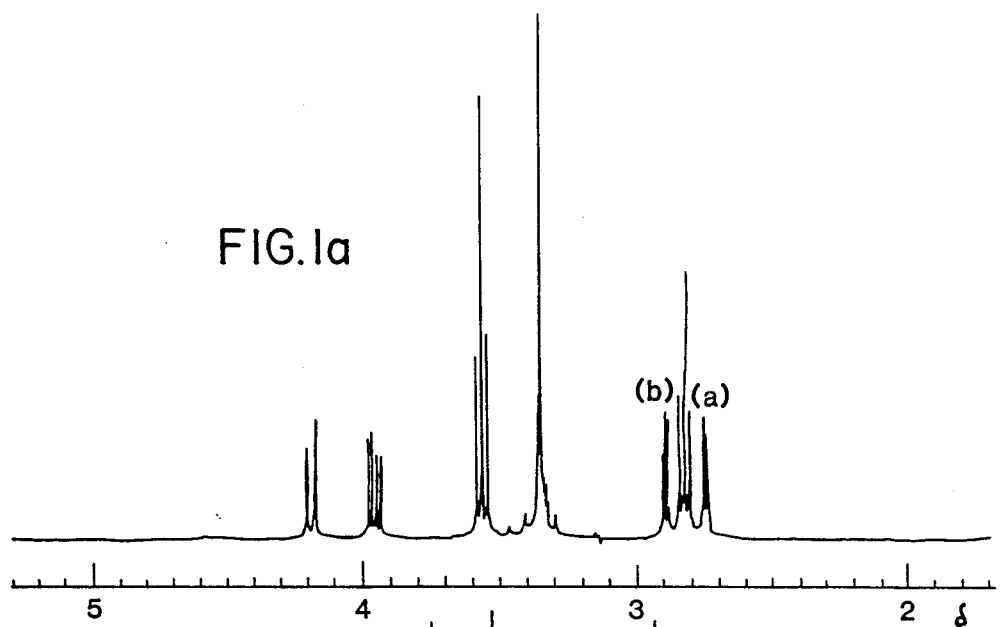

In the following examples there are described several preferred embodiments to illustrate the invention. However, it should be understood that the invention is not intended to be limited to the specific embodiments.

EXAMPLE 1

Transformation of 4-(2-methoxyethyl)-phenyl allyl ether into (+)-4-(2-methoxyethyl)-phenyl glycidyl ether by Rhodococcus equi

NCIB 12035

Approximately half the biomass from a 72 hour culture of *Rhodococcus equi* NCIB 12035 grown at 30° C. on tetradecane (1 ml) in 100 ml of ASM mineral salts medium containing 0.02% of yeast extract was transferred to a 250 ml conical flask containing 50 ml of ASM, 0.02% of yeast extract, 0.15 ml of tetradecane, 1 ml of octane, 0.05 ml of Tween 80 and 0.05 ml of 4-(2-methoxyethyl)phenyl allyl ether. The contents were incubated at 30° C. on an orbital shaker and samples were extracted with methylene chloride prior to analysis by gas chromatography on a Varian 3700. [Column 3%OVI on WHP 100–120, 50 cm×2 mm i.d., 100° C.–200° C. at 10° C./min, $N_2$ at 30 cc/min]. ASM contains 0.535 g/l of $NH_4Cl$, 0.531 g/l of $KH_2PO_4$, 0.866 g/l of $Na_2HPO_4$, 0.174 g/l of $K_2SO_4$, 0.037 g/l of $MgSO_4.7H_2O$, 0.00735 g/l of $CaCl_2.2H_2O$, 1.0 ml/l of $TK_3$ trace elements and 1.0 ml of a 0.1 M solution/l of $FeSO_4.7H_2O$, $TK_3$ contains 0.288 g/l of $ZnSO_4.7H_2O$, 0.224 g/l of $MnSO_4.4H_2O$, 0.0618 g/l of $H_3BO_3$, 0.1248 g/l of $CuSO_4.5H_2O$, 0.0484 g/l of $Na_2MoO_4.2H_2O$, 0.0476 g/l of $CoCl_2.6H_2O$, 0.083 g/l of KI, 1 ml/l of 1 M $H_2SO_4$ at pH 7.0.

The product, (+)-4-(2-methoxyethyl)-phenyl glycidyl ether, appeared after 48 hours incubation and increased until 96 hours when the level of epoxide was approximately 15% of the remaining 4-(2-methoxyethyl)-phenyl allyl ether. To accumulate sufficient quantities of (+)-4-(2-methoxyethyl)-phenyl glycidyl ether, the culture broth from 10×50 ml and 5×500ml incubation (conditions as described above) was extracted with 350 ml of methylene chloride. The extract was dried over $Na_2SO_4$, the solvent evaporated, and the epoxide was purified on silica gel using a hexane/ether gradient (epoxide eluted with 30% ether) to obtain 353 mg of (+)-4-(2-methoxyethyl)-phenyl glycidyl ether having $[\alpha]D^{25} = +8.11°$ (c=0.95 in ethanol).

Figure 1B:
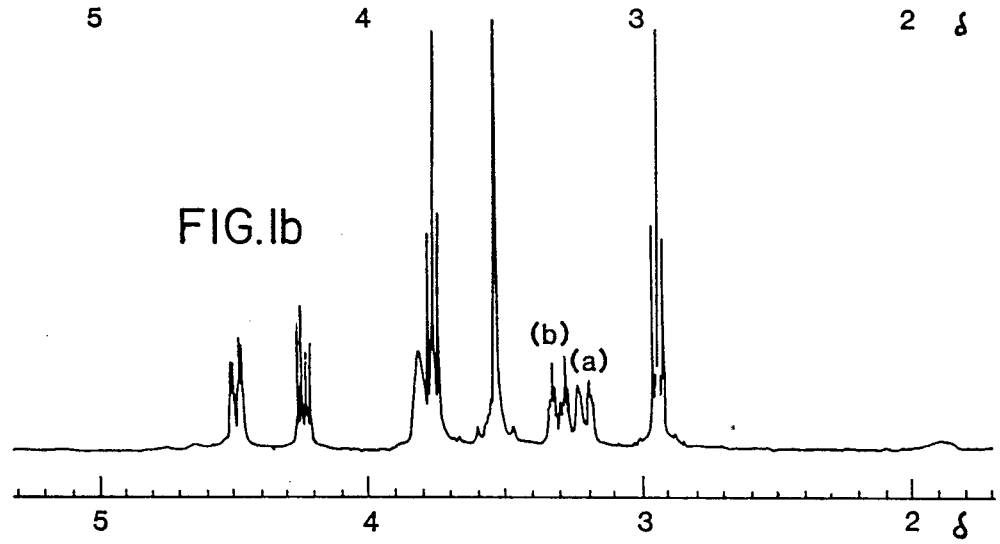
Figure 1C:
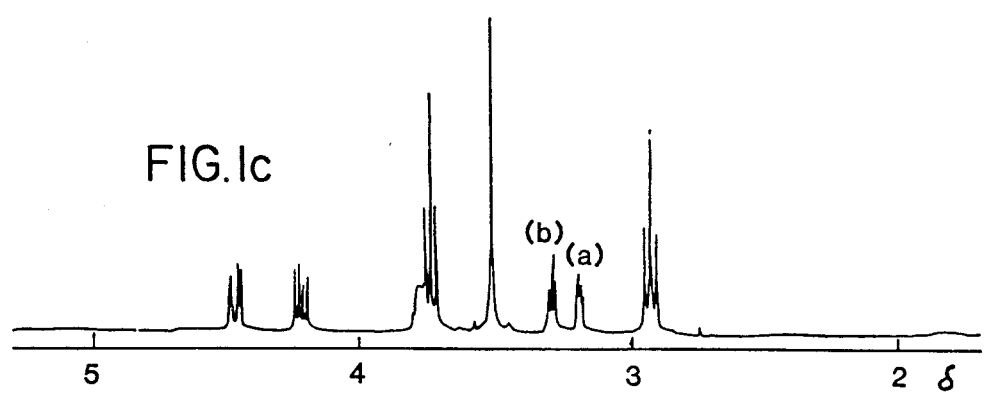

Optical purity of (+)-4-(2-methoxyethyl)-phenyl glycidyl ether was investigated using pmr in the presence of europium shift reagent $E\mu$ hfc)3 (see FIG. 1). On addition of the shift reagent, the envelope of signals from each of the geminal protons labelled (a) and (b) in the chemically synthesised (±)-4(2-methoxyethyl)-phenyl glycidyl ether (FIG. 1A) shifted downfield and each was split into two envelopes of signals of equal intensity [FIG. 1B, (a)+(b)]. However, under the same conditions, only on envelope of signals was detectable from each of the geminal proton in the microbially produced (+)-4-(2-methoxyethyl)-phenyl glycidyl ether [FIG. 1C, (a)+(b)]. Thus, the optical purity of the (+)-4-(2-methoxyethyl)-phenyl glycidyl ether obtained by microbial epoxidation was determined to be 100%, within the experimental error of the pmr measurements.

EXAMPLE 2

Conversion of (+)-4-(2-methoxyethyl)-phenyl glycidyly ether into (−)-metoprolol

Figure 2:
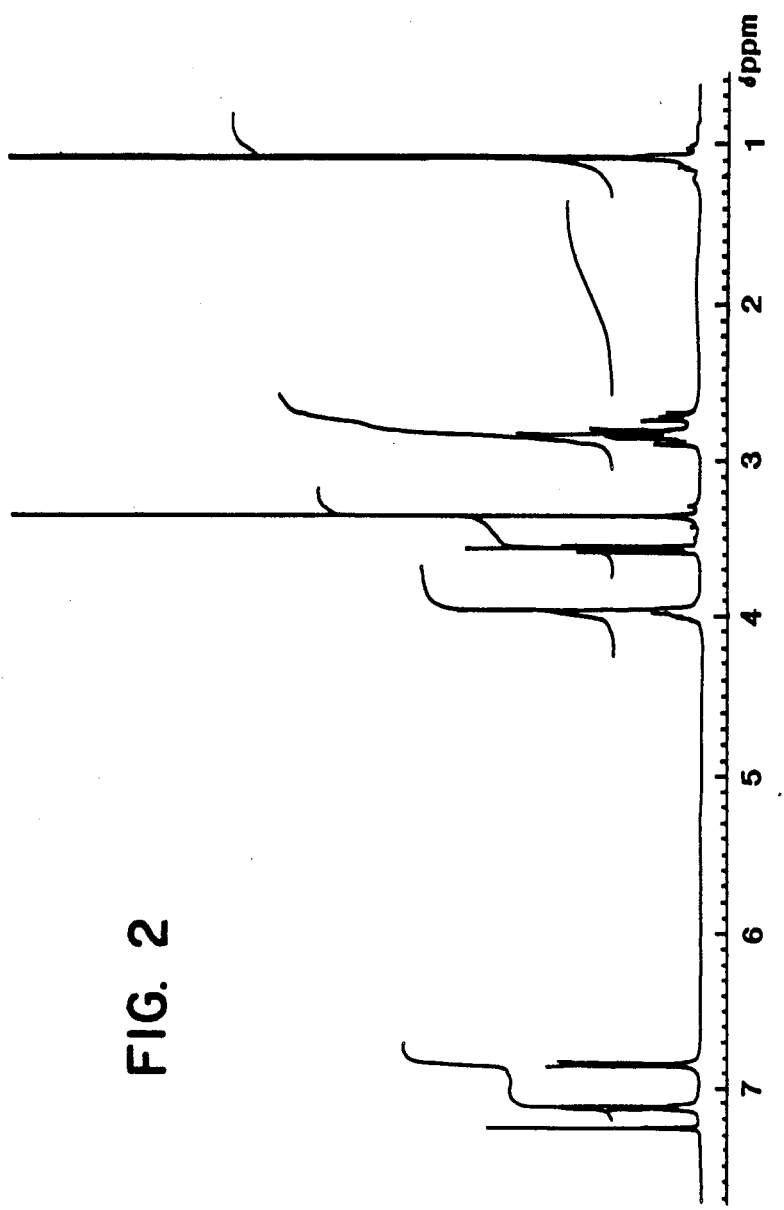
FIG. 2 shows the pmr spectrum of (−)-metoprolol
Figure 3:
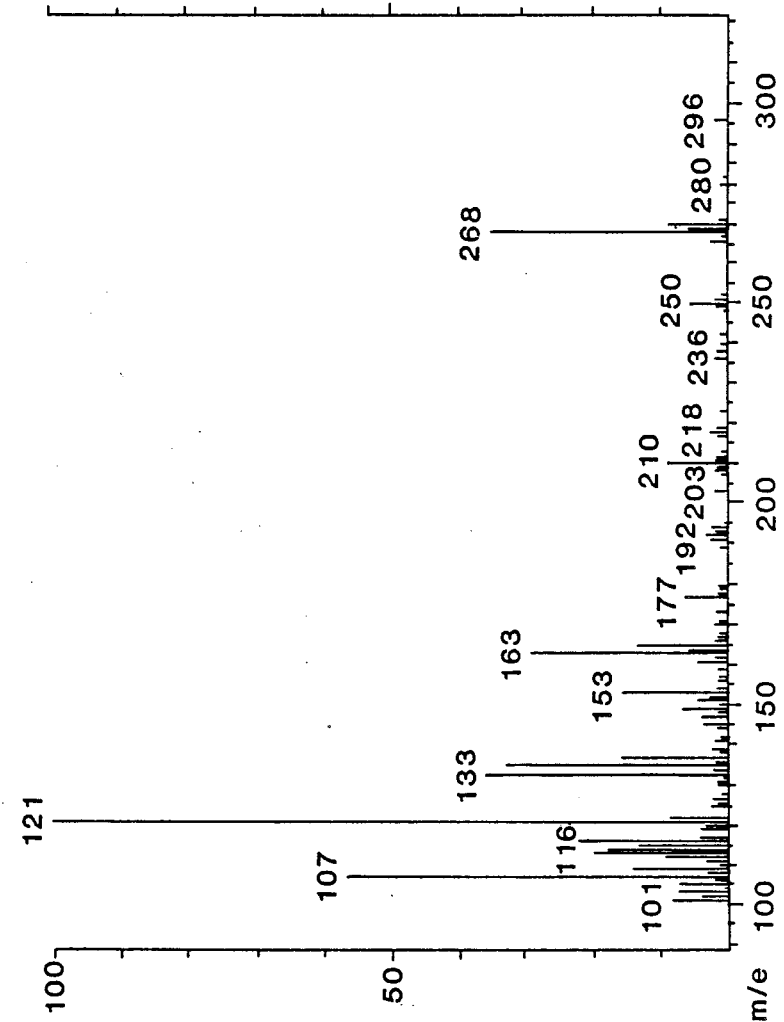
FIG. 3 shows the mass spectrum determined by C.I. ($CH_4$) of (−)-metoprolol.

A solution of 290 mg of (+)-4-(2-methoxyethyl)-phenyl glycidyl ether of Example 1 in 6.2 ml of dried ethanol containing 1.84 ml of isopropylamine was heated at reflux for 3 hours after which the sovents were removed by evaporation The resulting oil was dissolved in 10 ml of methylene chloride and the solution was extracted with 10 ml of 0.2N HCl which was then washed twice with 10 ml of methylene chloride. The acid layer was made basic with 3 ml of 2N NaOH and the product was extracted with 10 ml of methylene chloride. The methylene chloride extract was dried over $Na_2SO_4$ and the solvent was evaporated to obtain a sticky solid. The product was crystallized from hexane to obtain 260 mg of (−)metoprolol having a $[\alpha]D^{25} = -5.46°$ (c=1.01 in ethanol) and melting at 42–45° C. (±)-metoprolol melting at 49–51° C., prepared chemically was, as expected, optically inactive. The pmr and mass spectra of (−)-metoprolol (FIGS. 2 and 3) and (±)-metoprolol (not shown) were consistent with the required structure and were indistinguishable from the pmr spectrum of (±)-meto prolol (melting at 48.5–50.5° C.) extracted from a commercial sample of metoprolol tartrate.

Optical purity of the (−)-metoprolol was determined by separation of its S-leucyldiastereomeric amide derivatives on a reverse phase HPLC column [Lichrosorb RP8 110 μm), 25 cm×¼ o.d., 4.9 mm i.d., mobile phase: 40% acetonitrile in 0.1 M Na phos phate buffer pH 3.0 to 2.5 ml/min., U.V. detection]. Derivatization was achieved by reacting metoprolol with the symmetrical anhydride of tertiary-butoxycarbonyl-S-leucine (BOC-S-leucine). followed by removal of the BOC group with trifluoroacetic acid as described by Hermansson et al [J. Chrom., Vol. 227, p. 113 (1982)] Analysis of a sample derived from the (±)-metoprolol resulted in two peaks of equal intensity as expected for a racemate The sample derived from the (−)-metoprolol gave two peaks with intensity ratio 97.7 : 2.3, equivalent to an optical purity of 95.4%.

EXAMPLE 3

Transformation of 4-(2-methoxyethyl)-phenyl glycidyl allyl ether into (+)-4-(2-methoxyethyl)-phenyl glycidyl ether by *Pseudomonas aeruginosa* NCIB 12036 followed by its transformation into (−)-metoprolo A suspension of *Pseudomonas aeruginosa* NCIB 12036 was prepared by resuspending cells which had been grown in an ASM mineral salts medium containing 0.75% Na lactate and 0.05% diethoxy methane for 24 hours at 30° C. in ASM to a volume equal to one tenth of the original culture volume.

1100 ml of cell suspension were incubated with 3.3 g of 4-(2-methoxyethyl)-phenyl allyl ether at 30° C. at 220 rpm. After 24 hours, the reaction mixture was extracted with 500 ml of methylene chloride and the extract was dried over $Na_2SO_4$, and the solve was evaporated to obtain 2.67 g of an oil. Purification on silica gel as in Example 1 yielded 930 mg of (+)-4-(2-methoxyethyl)-phenyl glycidyl ether with $[\alpha]D^{25}= +8.21°$ (c=0.943 in ethanol).

Optical purity, as measured by pmr in the presence of europium shift reagent $E\mu$ (hfc)3 as in Example 1 was determined to be 100% within the experimental error of the pmr measurements. 694 mg of (+)-4-(2-methoxyethyl)-phenyl glycidyl ether were used (method as in Example 2) to prepare 579 mg of (−)-metoprolol melting at 44–46° C. with $[\alpha]D^{25}= -5.49°$ (c =1.02 in ethanol). Optical purity was determined to be 98% (method as in Example 2). The mother liquor was crystallized to obtain 113 mg of (−)-metoprolol with an optical purity of 96%.

EXAMPLE 4

Transformation of 4-(2-methoxyethyl )-phenyl allyl ether into (+)-4-(2-methoxyethyl)-phenyl glycidyl ether by Pseudomonas aeruginosa NCIB 8704 followed by its transformation into (−)-metoprolol 200 ml of cell suspension of Pseudomonas aeruginosa NCIB 8704 prepared as described in Example 3 were incubated with 2 g of 4-(2-methoxyethyl)-phenyl allyl ether at 30° C. for 24 hour after which the suspension was extracted and purified as in Example 3 to obtain 91 mg of (+)-4-(2-methoxyethyl)-phenyl glycidyl ether. Optical purity of the epoxide, measured by pmr in the presence of europium shift reagent $E\mu$ (hfc 3 as in Example I was determined to be 100% within the errors of the pmr measurements.

76 mg of (+)-4-(2-methoxyethyl)-phenyl glycidyl ether were used (method as in Example II) to prepare 55 mg of (−)-metoprolol melting at 42–45° C. with a $[\alpha]D^{25}= -4.93°$ (c =0.944 in ethanol), with an optical purity of 98.8% as determined by HPLC o its S-leucyl diastereomeric derivatives as in Example 2 . Evaporation of the mother liquor yielded 17 mg of (−)-metoprolol of optical purity.

EXAMPLE 5

Transformation of 4-(2-methoxyethyl)-phenyl allyl ether into (+)-4-(2-methoxyethyl)-phenyl glycidyl ether by Pseudomonas putid NCIB 9571 followed by its transformation into (−)-metoprolol 200 ml of cell suspension of *Pseudomonas outida* NCIB 9571 prepared as in Example 3 was incubated with.1 g of 4-(2methoxyethyl)phenyl allyl ether at 30° C. for 24 hours, after which it was extracted with methylene chloride and purified as in Example 3 to obtain 324 mg of (+)-4-(2-methoxyethyl)-phenyl glycidyl ether with $[60]D^{25} = +6.42°$ (c =0.88 in ethanol). Optical purity as measured by pmr in the presence of europium shift reagent $E\mu$ (hfc)3 as in Example 1 was 100% within the experimental errors of the pmr measurements.

214 mg of (+)-4-(2-methoxyethyl)-phenyl glycidyl ether were condensed with isopropylamine as in Example 2 to obtain 146 mg of (−)-metoprolol melting at 44–46° C. with $[\alpha]D^{25} = -5.00°$ (c=1.01 in ethanol). Optical purity (method as in Example 2) was determined to be 98%. Evaporation of the mother liquor yielded 9 mg of (−)-metoprolol of 97.5% optical purity.

EXAMPLE 6

Transformation of 4-(2-methoxyethyl)-phenyl allyl ether into (+)-4-(2-methoxyethyl)-phenyl glycidyl ether by *Pseudomonas oleovorans* ATCC 29347 followed by its transformation into (−)-metoprolol 200 ml of cell suspension of *Pseudomonas oleovorans* ATCC 29347 prepared as in Example 3 were incubated with 2 g of 4-(2-methoxyethyl)-phenyl allyl ether at 30° C. for 5hours. Extraction with methylene chloride and purification-on silica gel as in Example 1 yielded 289 mg of (+)-4-(2-methoxyethyl)-phenyl glycidyl ether with $[\alpha]D^{25} = +8.02°$ (c =1.16 in ethanol). Optical purity as measured by pmr in the presence of europium shift reagent $E\mu$ (hfc)3 as in Example 1 was determined to be 100% within the experimental errors of the pmr measurements.

171 mg of (+)-4-(2-methoxyethyl)-phenyl glycidyl ether were reacted with isopropylamine (method as in Example 2) to obtain 154 mg of (−)-metoprolol melting at 44–45° C. with $[\alpha]D^{25} = -5.27°$ (c =0.967 in ethanol). Optical purity was determined to be 98.4% based on HPLC of the S-leucyl diastereomeric derivatives as in Example 2. Evaporation of the mother liquor gave 6 mg of (−)-metoprolol of 92.2% optical purity.

EXAMPLE 7

Microbial transformation of 4-(2-methoxyethyl)-phenyl allyl ether into (+)-4-(2-methoxyethYl)-phenyl glycidyl ether 50 ml of mineral salts medium containing 0.05 ml of Tween 80, 0.05 m.1 of tetradecane and 0.05 ml of 4-(2-methoxyethyl) phenyl allyl ether were inoculated with either *Nocardia corallina* ATCC 31338, *Rhodococcus sp* NCIB 11277 or *Mycobacterium rhodochrou* (*Rhodococcus sp*) NCIB 9703 (all pregrown for 72 hours on 0.5% tetradecane), then incubated at 30° C. Samples taken at 24 hours and 96 hours were extracted with methylene chloride and analyzed by ga chromatography (GC).

In each case, peaks corresponding to 4-(2-methoxyethyl -phenyl glycidyl ether were detected with conversions as follows: *Mycobacterium rhodochrous* 2% after 24 hours; *Rhodococcus sp.* 1% after 96 hours and *Nocardia corallina* 5% after 96 hours. Further confirmation of the structure was obtained when the contents of a scaled up experiment using *Nocardia corallina* (500 ml culture, conditions as above) were extracted with methylene chloride followed by purification on silica gel and pmr analysis. The pmr europium shift spectra of the 4-(2-methoxyethyl)-phenyl glycidyl ether suggested an optical purity of 100%, and were identical to the europium pmr spectra of (+)-4-(2-methoxyethyl)-phenyl glycidyl ether obtained from *Rhodococcus equi*.

EXAMPLE 8

Transformation of 4-(2-methoxyethyl)-phenyl allyl ether into 4(2-methoxyethyl)-phenyl qlycidyl ether by *Pseudomonas oleovorans* ATCC 29347

A suspension of *Pseudomonas oleovorans* ATCC 29347 was prepared by resuspending cells [which had been grown to stationary phase in PSX mineral salts medium at a pH 7 containing 0.75% glycerol and 0.05% diethoxymethane at 30° C.] in PSX at a pH of 7.5, to a volume equal to one tenth of the original culture volume. 10 ml (dry weigh 12.6 g/l contained in a 250 ml conical flask-)of a cell suspension were incubated with 250 $\mu$l of 4-(2-methoxyethyl)-phenyl allyl ether and 50 mg of glucose at 37° C. on an orbital shaker, Formation of 4-(2-methoxyethyl)-phenyl glycidyl ether was monitored by after extraction with methylene chloride (conditions as described in previous examples). The level of 4-(2-methoxyethyl)phenyl glycidyl ether in the incubation mixture was 7.30 g/l after six hours.

Various modifications of the process of the invention may be made without departing from the spirit or scope thereof and it should be understood that the invention is intended to be limited only as defined in the appended claims.

What we claim is:

1. A process for the preparation of metoprolol in a stereo-specific form or a non-toxic, pharmaceutically acceptable acid addition salt thereof and/or a sterospecific form of 4-(2-methoxyethyl)-phenyl glycidyl ether which comprises subjecting 4-(2-methoxyethyl)-phenyl allyl ether to the action of a microorganism selected from the group consisting of *Nocardia corallina* (ATCC 31338); *Rhodococcus sp* (NCIB 11277); *Mycobactyeriaum rhodochrous* (NCIB 9703); *Rhodococcus equi* (NCIB 12035); *Pseudomonas aeruginosa* (NCIB 12036); *Pseudomonas oleovorans* (ATCC 29347); *Pseudomonas putida* (NCIB 9571) and *Pseudomonas Aeruginosa* (NCIB 8704) having the ability for sterio-selective epoxidation of 4-(2-methoxyethyl)-phenyl allyl ether into 4-(2-methoxyethyl)-phenyl glycidyl ether having at least 80% by weight the S configuration, at least partly separating 4-(2-methoxyethyl)-phenyl glycidyl ether with isopropylamine and at least partly separating metroprolol and/or converting metoprolol into the non-toxic, pharmaceutically acceptable acid addition salts.

2. The process of claim 1 wherein said bacteria is are able to convert 4-(2-methoxyethyl)-phenyl allyl ether into 4-(2-methoxyethyl)-phenyl glycidyl ether having at least 90% by weight the S configuration.

3. The process of claim 1 wherein the bacteria used is *Nocardia corallina* (ATCC 31338).

4. The process of claim 1 wherein the bacteria used is *Rhodococcus sp* (NCIB 11277).

5. The process of claim 1 wherein the bacteria used is *Mycobacteriaum rhodochrous* (NCIB 9703).

6. The process of claim 1 wherein the bacteria used is *Rhodococcus equi* (NCIB 12035).

7. The process of claim 1 wherein the bacteria used is *Pseudomonas aeruginosa* (NCIB 12036).

8. The process of claim 1 wherein the bacteria used is *Pseudomonas oleovorans* (ATCC 29347).

9. The process of claim 1 wherein the bacteria used is *Pseudomonas putida* (NCIB 9571).

10. The process of claim 1 wherein the bacteria used is *Pseudomonas Aeruginosa* (NCIB 8704).

11. A process for the preparation of 4-(2-methoxyethyl)-phenyl glycidyl ether having at least 80% by weight of S configuration comprising subjecting 4-(2-methoxyethyl)-phenyl allyl ether to the action of bacteria of claim 1 capable of stereoselectively epoxidizing the same.

12. A process for the preparation of metoprolol into a stereospecific form comprising subjecting 4-(2-methoxyethyl)-phenyl allyl ether to the action of a bacteria selected from the group consisting of *Nocardia corallina* (ATCC 31338); *Rhodococcus sp* (NCIB 11277); *Mycobacteriaum rhodochrous* (NCIB 9703); *Rhodococcus equi* (NCIB 12035); *Pseudomonas aeruginosa* (NCIB 12036); Pseudomonas oleovorans (ATCC 29347); Pseudomonas putida (NCIB 9571) and *Pseudomkonas Aeruginosa* (NCIB 8704) having the ability for stereoselective epoxidation of 4-(2-methoxyethoxy)-phenyl allyl ether into 4-(2-methoxyethyl)-phenyl glycidyl ether having at least 80% by weight the S configuration, reacting 4-(2-methoxyethyl)-phenyl glycidyl ether with isopropylamine and at least partly separating metoprolol.

13. The method of claim 12 wherein metoprolol is converted into its non-toxic, pharmaceutically acceptable acid addition salt.

* * * * *

UNITED STATES PATENT AND TRADEMARK OFFICE
CERTIFICATE OF CORRECTION

PATENT NO. : 4,956,284

DATED : Sept. 11, 1990

INVENTOR(S) : Gareth T. Phillips, et al

It is certified that error appears in the above-identified patent and that said Letters Patent is hereby corrected as shown below:

Col. 8, Claim 1, line 54, after "ether" insert --and/or reacting 4-(2-methoxyethyl)-phenyl glycidyl ether--.

Signed and Sealed this

Nineteenth Day of January, 1993

Attest:

DOUGLAS B. COMER

Attesting Officer

Acting Commissioner of Patents and Trademarks